United States Patent
Kawasaki et al.

(10) Patent No.: US 11,648,189 B2
(45) Date of Patent: May 16, 2023

(54) FOAMABLE AEROSOL COMPOSITION

(71) Applicant: NIPPON PAPER INDUSTRIES CO., LTD., Kita-ku (JP)

(72) Inventors: Takafumi Kawasaki, Tokyo (JP); Takeshi Nakatani, Tokyo (JP); Noriko Motoyama, Ibaraki (JP)

(73) Assignee: NIPPON PAPER INDUSTRIES CO., LTD., Kita-ku (JP)

(*) Notice: Subject to any disclaimer, the term of this patent is extended or adjusted under 35 U.S.C. 154(b) by 0 days.

(21) Appl. No.: 16/309,518

(22) PCT Filed: Jun. 15, 2017

(86) PCT No.: PCT/JP2017/022202
§ 371 (c)(1),
(2) Date: Dec. 13, 2018

(87) PCT Pub. No.: WO2017/217511
PCT Pub. Date: Dec. 21, 2017

(65) Prior Publication Data
US 2019/0224083 A1    Jul. 25, 2019

(30) Foreign Application Priority Data

Jun. 16, 2016 (JP) ............................. JP2016-119787

(51) Int. Cl.
*A61K 8/04* (2006.01)
*A61Q 19/00* (2006.01)
*A61K 8/02* (2006.01)
*A61K 8/73* (2006.01)
*C09K 3/00* (2006.01)
*B65D 83/28* (2006.01)
*B65D 83/14* (2006.01)
*C08B 11/12* (2006.01)
*C08B 15/04* (2006.01)

(52) U.S. Cl.
CPC ............... *A61K 8/046* (2013.01); *A61K 8/02* (2013.01); *A61K 8/73* (2013.01); *A61K 8/731* (2013.01); *A61Q 19/00* (2013.01); *B65D 83/285* (2013.01); *B65D 83/752* (2013.01); *C09K 3/00* (2013.01); *A61K 2800/413* (2013.01); *A61K 2800/805* (2013.01); *A61K 2800/87* (2013.01); *C08B 11/12* (2013.01); *C08B 15/04* (2013.01)

(58) Field of Classification Search
CPC . A61K 8/02; A61K 8/046; A61K 8/73; A61K 8/731; A61K 2800/413; A61K 2800/805; A61K 2800/87; A61Q 19/00; B65D 83/285; B65D 83/752; C09K 3/00; C08B 11/12; C08B 15/04
See application file for complete search history.

(56) References Cited

U.S. PATENT DOCUMENTS

| | | | |
|---|---|---|---|
| 9,801,802 B2 | 10/2017 | Isogai et al. | |
| 9,901,527 B2 | 2/2018 | Isogai et al. | |
| 2010/0189857 A1 | 7/2010 | Blijdenstein et al. | |
| 2011/0150804 A1* | 6/2011 | Nojiri | A61K 8/365 424/70.1 |
| 2012/0308624 A1* | 12/2012 | Isogai | A61K 8/027 424/401 |
| 2013/0078191 A1 | 3/2013 | Teramoto et al. | |
| 2015/0368541 A1* | 12/2015 | Monclin | C09K 8/64 507/108 |
| 2016/0333116 A1* | 11/2016 | Nakatani | C08B 11/12 |

FOREIGN PATENT DOCUMENTS

| | | | | |
|---|---|---|---|---|
| CN | 102724955 A | 10/2012 | | |
| EP | 2 628 395 A1 | 8/2013 | | |
| JP | 2006-180717 A | 7/2006 | | |
| JP | 2006-342119 A | 12/2006 | | |
| JP | 2007-326809 A | 12/2007 | | |
| JP | 2010-18645 A | 1/2010 | | |
| JP | 2016-65030 A | 4/2016 | | |
| JP | 2016-69623 A | 5/2016 | | |
| WO | WO 2010/121490 A1 | 10/2010 | | |
| WO | WO 2011/089709 A1 | 7/2011 | | |
| WO | WO-2014088072 A1 * | 6/2014 | | |
| WO | WO-2014154348 A1 * | 10/2014 | | C09K 8/035 |
| WO | WO 2015/107995 A1 | 7/2015 | | |
| WO | WO-2015107995 A1 * | 7/2015 | | |

OTHER PUBLICATIONS

English translation of WO-2014088072-A1 from Google Patents. Translated on Oct. 23, 2019. (Year: 2019).*
International Search Report dated Sep. 12, 2017 in PCT/JP2017/022202 filed on Jun. 15, 2017.
Combined Indian Office Action and Search Report dated Oct. 31, 2019, in Patent Application No. 201947000948, 6 pages.
Extended European Search Report dated Dec. 13, 2019 in Patent Application No. 17813405.2, 10 pages.
Cervin, N.T. et al. "Lightweight and Strong Cellulose Materials Made from Aqueous Foams Stabilized by Nanofibrillated Cellulose" Biomacromolecules, vol. 14, No. 2, XP055245485, Dec. 2012, 9 Pages.
Combined Chinese Office Action and Search Report dated Feb. 23, 2021 in Chinese Patent Application No. 201780036238.1, 11 pages.

* cited by examiner

*Primary Examiner* — Doan T Phan
(74) *Attorney, Agent, or Firm* — Oblon, McClelland, Maier & Neustadt, L.L.P.

(57) ABSTRACT

An object is to provide a foamable aerosol composition that can be continuously ejected from the container to form dense and uniform foam, and that the formed foam has certain elasticity as well as can be easily spread on an object, and the foamable aerosol composition comprises a stock solution including cellulose nanofibers and a propellant is provided.

9 Claims, No Drawings

FOAMABLE AEROSOL COMPOSITION

TECHNICAL FIELD

The present invention relates to a foamable aerosol composition.

BACKGROUND ART

Aerosol products generally consist of a liquid for intended used (stock solution), a propellant (for example, liquefied gas or compressed gas), and a container for enclosing these stock solution and propellant, wherein the container has a structure of discharging the stock solution to the outside by the pressure of the propellant. The container usually includes an actuator, and discharged amounts of the stock solution and gas can be controlled by operating the actuator. Moreover, the stock solution is sealed in the container, and thus is sanitary and no waste. Due to these advantages, the aerosol products are used as household products such as deodorants, fragrances, cleaners, and waxes, personal products such as cosmetics and medicines, paint products, insecticidal products, industrial products such as metal flaw detection agents and antirust agents, and automobile products. Hereinafter, the stock solution and the propellant are also collectively referred to as an aerosol composition.

Among the aerosol compositions, a foamable aerosol composition to be taken in the foam state (foam) at the time of being discharged from the container has characteristics such that the composition is difficult to scatter, difficult to drip even when being discharged on a ceiling, a wall, or the like, difficult to dry even when being left for a long time, easy to spread on necessary parts, easy to remove stains by making it float up, excellent in heat insulating properties, as compared with the composition to be taken in the mist state (mist or spray). Therefore, by utilizing such characteristics, the foamable aerosol composition is used for various applications (for example, window cleaner, hair styling foam, shaving foam, face wash foam, facial treatment mask, and urethane foam insulation).

For example, an aerosol composition including edible fat and oil, vinegar, specific emulsifier, and xanthan gum has been used as foam-containing dressing, which well adheres to food (Patent Document 1).

Moreover, an aerosol composition including polyethylene glycol having a specific degree of polymerization and ethyl cellulose has been known (Patent Document 2).

Furthermore, an aerosol type hair color composition including hydroxyethyl cellulose as a polysaccharide type polymer has been known (Patent Document 3).

Incidentally, there has been known a post-foamable aerosol composition that does not foam immediately after ejecting from a container and gradually foams after ejecting, though it is not an aerosol composition. For example, there has been a post-foamable aerosol composition including cellulose fine particles having an average particle diameter of 5 µm or less, an average degree of polymerization (DP) of 100 or less, and a crystallization ratio of 50% or less and a nonionic surfactant (Patent Document 4).

PRIOR ART DOCUMENTS

Patent Documents

Patent Document 1: JP-A-2006-180717
Patent Document 2: JP-A-2006-342119
Patent Document 3: JP-A-2007-326809
Patent Document 4: JP-A-2010-018645

SUMMARY OF INVENTION

Problem to be Solved by the Invention

Examples of performances required for the foamable aerosol composition at the time of being discharged from the container include that foam is continuously discharged and that the composition forms dense and uniform foam. In addition, examples of performances after discharge include that the composition is difficult to be a liquid state due to disappearance of foam, that the foam has certain elasticity as well as is hard to drip, and that the foam is easy to spread on the object.

In the techniques described in Patent Documents 1 to 3, improvement of any of the above performances is intended by including a thickener such as xanthan gum or hydroxyethyl cellulose (HEC) in the foamable aerosol composition. The improvement, however, is not sufficient.

Moreover, the technique in Patent Document 4 relates to the post-foamable aerosol composition and does not improve the performance required for the foamable aerosol composition.

The foamable aerosol composition being continuously ejected to form dense and uniform foam, and having good elasticity and applicability to an object still has been desired.

Means for Solving Problem

As a result of extensive research to solve the above problems, the inventors of the present invention have found that the above problems can be solved by adding cellulose nanofibers into the stock solution and have completed the present invention.

Accordingly, the present invention provides the followings.

[1] A foamable aerosol composition, comprising: a stock solution comprising a cellulose nanofiber and a propellant.

[2] The foamable aerosol composition according to [1], wherein the content ratio of the cellulose nanofiber is from 0.001 to 10% by mass relative to the total amount of the stock solution.

[3] The foamable aerosol composition according to [1] or [2], wherein the cellulose nanofiber comprises a chemically modified cellulose nanofiber.

[4] The foamable aerosol composition according to [3], wherein the chemically modified cellulose nanofiber is one or more kinds selected from an oxidized cellulose nanofiber and an etherified cellulose nanofiber.

[5] The foamable aerosol composition according to [4], wherein the amount of a carboxy group contained in the oxidized cellulose nanofiber is from 0.1 mmol/g to 3.0 mmol/g relative to a bone-dry mass of the oxidized cellulose nanofiber.

[6] The foamable aerosol composition according to [4], wherein the etherified cellulose nanofiber is a carboxymethylated cellulose nanofiber.

[7] The foamable aerosol composition according to [6], wherein a degree of substitution with carboxymethyl group per glucose unit in the carboxymethylated cellulose nanofiber is from 0.01 to 0.50.

[8] The foamable aerosol composition according to any one of [1] to [7], wherein the foamable aerosol composition is a facial treatment mask.

[9] A kit, comprising: an aerosol container and the foamable aerosol composition according to any one of [1] to [8] filled in the aerosol container.

Effect of the Invention

According to the present invention, it can provide the foamable aerosol composition that can be continuously ejected from the container to form dense and uniform foam, and that the formed foam has certain elasticity as well as can be easily spread on an object. Moreover, the foamable aerosol composition of the present invention serving as a facial treatment mask has good adsorbability to skin.

EMBODIMENTS FOR CARRYING OUT THE INVENTION

<<A>> Foamable Aerosol Composition of the Present Invention

The foamable aerosol composition of the present invention includes at least a stock solution including cellulose nanofibers and a propellant, and preferably consists of a stock solution including cellulose nanofibers and a propellant. The foamable aerosol composition of the present invention may further include other additives, if needed. Hereinafter, the foamable aerosol composition will be described in detail.

<Propellant>

The foamable aerosol composition of the present invention includes the propellant. The kinds of the propellant are not particularly limited, and may include the propellant usually used in aerosol products. Examples of the propellant include Freon, liquefied petroleum gas, dimethyl ether, nitrogen, carbon dioxide gas, oxygen, air, helium, and argon. The propellant may be used singly or in combination of two or more propellants. Among these propellants, one or more propellants selected from liquefied petroleum gas and carbon dioxide gas are preferable from the viewpoint of foamability and a foaming property.

The content ratio of the propellant is not particularly limited, and the content ratio is preferably 1 to 60% by mass relative to the foamable aerosol composition.

<Stock Solution>

The stock solution included in the foamable aerosol composition is a component excluding the propellant among the components to be sealed in the container. The content ratio of the stock solution is preferably 40 to 99% by mass relative to the foamable aerosol composition. The stock solution includes cellulose nanofibers.

[1. Cellulose Nanofiber]

In the present invention, the cellulose nanofibers are fine fibers of unmodified cellulose or chemically modified cellulose. The cellulose nanofibers usually have an average fiber diameter about from 3 to 500 nm, and preferably from 3 nm or more and to 500 nm or less. Moreover, the cellulose nanofibers according to the present invention usually have an average aspect ratio of 10 or more. The upper limit of the aspect ratio is not particularly limited and usually 1000 or less.

The average fiber diameter and average fiber length of the cellulose nanofibers can be calculated as a number average fiber diameter or average fiber length by, for example, preparing a 0.001% by mass aqueous dispersion liquid of the cellulose nanofibers, thinly spreading this diluted dispersion liquid on a sample stage made of mica, drying by heating the sample at 50° C. to prepare a sample for observation, and measuring the sectional height of a shape image observed with an atomic force microscope (AFM). Moreover, the average aspect ratio can be calculated in accordance with the following formula:

$$\text{Average aspect ratio} = \text{Average fiber length} / \text{Average fiber diameter}$$

The cellulose nanofibers according to the present invention can be obtained by defibrating the cellulose raw material, by chemically modifying the cellulose raw material and thereafter defibrating the modified cellulose raw material, or by defibrating the cellulose raw material and thereafter chemically modifying the defibrated cellulose raw material. As the cellulose nanofibers according to the present invention, cellulose nanofibers produced by known methods can be used and commercially available products may be used.

As advantages of the cellulose nanofibers, the cellulose nanofibers have what is called thixotropy in which, in a dispersion liquid, the cellulose nanofibers exhibit a high apparent viscosity in a relatively low shear rate region, whereas the cellulose nanofibers exhibit a low viscosity in a relatively high shear rate region due to the pressure difference between the pressure of the propellant and the pressure of the outside air when the composition is ejected from the aerosol container. Accordingly, the foamable aerosol composition of the present invention is uniformly ejected during the ejection, and the viscosity of the stock solution is increased again after the ejection to retain the composition on the surface of the object to be ejected by including the cellulose nanofibers in the stock solution. Therefore, it is assumed that the following effects can be sufficiently exhibited: the foamable aerosol composition is hard to be a liquid state due to disappearance of the form; the foam has certain elasticity as well as is easily spread on the target object; and the foam is difficult to drip from the target object.

The content ratio of the cellulose nanofibers is preferably 0.001% by mass or more, more preferably 0.003% by mass or more, and further preferably 0.005% by mass or more relative to the total mass of the stock solution.

The content ratio of the cellulose nanofibers is preferably 10% by mass or less, more preferably 1% by mass or less, further preferably 0.5% by mass or less, further more preferably 0.3% by mass or less, particularly preferably 0.05% by mass or less or less than 0.05% by mass, and especially preferably 0.04% by mass or less, 0.03% by mass or less, 0.02% by mass or less, or 0.01% by mass or less relative to the total mass of the stock solution.

The content ratio of the cellulose nanofibers is preferably in a range of 0.001 to 10% by mass, more preferably in a range of 0.001 to 1% by mass, and further preferably 0.003 to 0.5% by mass relative to the total mass of the stock solution. When the content ratio of the cellulose nanofibers is 0.001% by mass or more relative to the total mass of the stock solution, the improving effect of the foam quality may be provided sufficiently. Moreover, when the content ratio is 10% by mass or less, retention time of the form and hardness of the foam may be appropriate. Consequently, the foamable aerosol composition of the present invention can be suitably used for various applications.

[1-1 Cellulose Raw Material]

The raw material of the cellulose nanofibers according to the present invention is not particularly limited and cellulose nanofibers can be produced from known cellulose raw materials. Examples of the cellulose raw material include raw materials derived from plants (for example, wood, bamboo, hemp, jute, kenaf, residue from agricultural land, cloth, pulps (a softwood unbleached kraft pulp (NUKP), a softwood bleached kraft pulp (NBKP), a hardwood unbleached kraft pulp (LUKP), a hardwood bleached kraft pulp (LBKP), a softwood unbleached sulfite pulp (NUSP), a bleached softwood sulfite pulp (NBSP), a thermomechanical pulp (TMP), a regenerated pulp, a used paper, and the like), raw materials derived from animals (for example, ascidians), raw materials derived from algae, raw materials derived from microorganisms (for example, acetic acid bacteria (*Acetobacter*)), and microbial products. The cellulose raw materials of the cellulose nanofibers according to the present invention may be any one of them or may be a combination of two or more kinds of them. The cellulose raw materials of the cellulose nanofibers according to the present invention are preferably cellulose fibers derived from plants or microorganisms, and more preferably cellulose fibers derived from plants.

The number average fiber diameter of the cellulose raw material used in the present invention is not particularly limited, and, in the case of the softwood kraft pulp and the hardwood kraft pulp that are general pulps, the former is about from 30 to 60 µm, and the latter is about from 10 to 30 µm, respectively. In the case of other pulps being subjected to general refining, the number average fiber diameter thereof is about 50 µm. For example, in the case of the ones obtained by refining raw materials having a size of several centimeters such as chips, it is preferable to adjust the number average fiber diameter thereof to about 50 µm by mechanically treating with a disintegrator such as a refiner and a beater.

[1-2 Dispersion]

In the case of subjecting the cellulose raw material to the defibration treatment or the modification treatment, the dispersion of the cellulose raw material may be prepared by subjecting the cellulose raw material to the dispersion treatment. The dispersion medium for dispersing the cellulose raw material is preferably water because the cellulose raw material is hydrophilic.

[1-3 Modification]

In the present invention, chemically modified cellulose nanofibers in which at least a part of cellulose constituting the fibers is chemically modified may be used as the cellulose nanofibers. Due to the chemical modification, the microfibrilation of the fibers are sufficiently advanced, and uniform fiber length and fiber diameter are obtained. Therefore, the effects of the present invention are easily exhibit. Accordingly, in the present invention, the chemically modified cellulose nanofibers are preferably used.

The modification method for obtaining the chemically modified cellulose nanofibers is not particularly limited. Examples of the method include oxidation, etherification, esterification, acetylation, silane coupling, fluorine modification, and cationization. Among them, oxidation, etherification, cationization, or esterification is preferable. Hereinafter, these modifications will be described.

[1-3-1 Oxidation]

In the present invention, in the case of using the cellulose nanofibers modified by oxidation (hereinafter, also referred to as oxidized cellulose nanofibers), the lower limit of the amount of the carboxy group in the oxidized cellulose nanofibers is preferably 0.1 mmol/g or more, more preferably 0.5 mmol/g or more, further preferably 1.0 mmol/g or more, and further more preferably 1.2 mmol/g or more relative to the bone-dry mass of the oxidized cellulose nanofibers. Moreover, the upper limit of the amount is preferably 3.0 mmol/g or less, more preferably 2.5 mmol/g or less, and further preferably 2.0 mmol/g or less. Therefore, the amount of the carboxy group in the oxidized cellulose nanofibers is preferably from 0.1 mmol/g to 3.0 mmol/g, more preferably from 0.5 mmol/g to 3.0 mmol/g, further preferably from 1.0 mmol/g to 2.5 mmol/g, and further more preferably from 1.2 mmol/g to 2.0 mmol/g relative to the bone-dry mass of the oxidized cellulose nanofibers.

Oxidation of the cellulose raw material or the cellulose fibers obtained after defibration of the cellulose raw material (hereinafter also referred to as defibrated cellulose fibers) can be carried out by known methods and is not particularly limited. However, the amount of carboxy group is preferably adjusted to be from 0.1 mmol/g to 3.0 mmol/g relative to the bone-dry mass of the cellulose fibers obtained by subjecting the cellulose raw material to the oxidation modification (hereinafter also referred to as oxidized cellulose fibers) or the oxidized cellulose nanofibers.

The oxidation method is not particularly limited. Example of the method is a method for oxidizing the cellulose raw material or defibrated cellulose fibers in water by using an oxidizing agent in the presence of an N-oxyl compound and a compound selected from the group consisting of a bromide, an iodide, and a mixture thereof. According to this oxidation method, the carbon atom having the primary hydroxy group at the C6 position of the glucopyranose ring on the cellulose surface is selectively oxidized to form a group selected from the group consisting of an aldehyde group, a carboxy group, and a carboxylate group on the surface. The concentration of the cellulose raw material during the reaction is not particularly limited, and is preferably 5% by mass or less.

The N-oxyl compound refers to a compound capable of generating a nitroxy radical. As the N-oxyl compound, any compound can be used as long as the compound accelerates the objective oxidation reaction.

The amount of the N-oxyl compound to be used is not particularly limited as long as the amount is a catalytic amount capable of the oxidizing cellulose being a raw material. For example, the lower limit of the amount is preferably 0.01 mmol or more, and more preferably 0.05 mmol or more relative to 1 g of the bone-dry mass of the cellulose. The upper limit of the amount is preferably 10 mmol or less, more preferably 1 mmol or less, and further preferably 0.5 mmol or less. Therefore, the amount of the N-oxyl compound to be used is preferably from 0.01 to 10 mmol, more preferably from 0.01 to 1 mmol, and further preferably from 0.05 to 0.5 mmol relative to 1 g of the bone-dry mass of the cellulose. Moreover, the amount is preferably about from 0.1 to 4 mmol/L relative to the reaction system.

The bromide is a compound containing bromine, and examples thereof include alkali metal bromides (such as sodium bromide and the like) capable of being ionized by dissociation in water. In addition, the iodide is a compound containing iodine, and examples thereof include alkali metal iodides. The amount of bromide or iodide to be used can be selected within a range capable of accelerating the oxidation reaction. The lower limit of the total amount of the bromide and the iodide is preferably 0.1 mmol or more, and more preferably 0.5 mmol or more relative to 1 g of the bone-dry mass of the cellulose. The upper limit thereof is preferably 100 mmol or less, more preferably 10 mmol or less, and further preferably 5 mmol or less. Therefore, the total amount of the bromide and the iodide is preferably from 0.1 to 100 mmol, more preferably from 0.1 to 10 mmol, and further preferably from 0.5 to 5 mmol relative to 1 g of the bone-dry mass of the cellulose.

The oxidizing agent is not particularly limited, and examples thereof include halogens, hypohalogeneous acids, halogeneous acids, perhalogeneous acids, salts thereof, halogen oxides, and peroxides. Among them, from the viewpoints of inexpensiveness and less environmental burden, the hypohalogeneous acids or the salts thereof are preferable, hypochlorous acid or the salt thereof is more preferable, and sodium hypochlorite is further preferable. The lower limit of the amount of the oxidizing agent to be used is preferably 0.5 mmol or more, more preferably 1 mmol or more, and further preferably 3 mmol or more relative to 1 g of the bone-dry mass of the cellulose. The upper limit of the amount is preferably 500 mmol or less, more preferably 50 mmol or less, further preferably 25 mmol or less, and most preferably 10 mmol or less. Therefore, the amount of the oxidizing agent to be used is preferably from 0.5 to 500 mmol, more preferably from 0.5 to 50 mmol, further preferably from 1 to 25 mmol, and most preferably from 3 to 10 mmol relative to 1 g of the bone-dry mass of the cellulose. Moreover, for example, the lower limit of the amount of the oxidizing agent to be used is preferably 1 mol or more relative to 1 mol of the N-oxyl compound. The upper limit of the amount is preferably 40 mol or less. Therefore, the amount of the oxidizing agent to be used is preferably from 1 to 40 mol relative to 1 mol of the N-oxyl compound.

Conditions such as pH, temperature, and reaction time during the oxidation reaction of the cellulose are not particularly limited, and, in general, the reaction proceeds efficiently even under relatively mild conditions. Therefore, the lower limit of the reaction temperature is preferably 4° C. or more, and more preferably 15° C. or more. The upper limit of the reaction temperature is preferably 40° C. or less, and more preferably 30° C. or less. Therefore, the reaction temperature is preferably from 4 to 40° C., and may be about from 15 to 30° C., that is, room temperature. The lower limit of the pH of the reaction solution is preferably 8 or more, and more preferably 10 or more. The upper limit of the pH is preferably 12 or less, and more preferably 11 or less. Therefore, the pH of the reaction solution is preferably from 8 to 12, and more preferably about from 10 to 11. The carboxy groups are generated in the cellulose with advancing the oxidation reaction, so that the pH of the reaction solution tends to decrease. Therefore, in order to efficiently promote the oxidation reaction, the pH of the reaction solution is preferably maintained within the above range by adding an alkaline aqueous solution such as an aqueous sodium hydroxide solution into the reaction solution. The reaction medium is preferably water from the viewpoints of easy handleability and difficulty in occurrence of side reactions.

The reaction time in the oxidation reaction can be appropriately set in accordance with the degree of progression of oxidation, and the lower limit is usually 0.5 hour or more. The upper limit is usually 6 hours or less, and preferably 4 hours or less. Therefore, the reaction time is usually about from 0.5 to 6 hours, and preferably about from 0.5 hour to 4 hours.

Moreover, the oxidation reaction may be carried out under two steps. For example, the oxidized cellulose obtained by filtering after the first step is oxidized again under the same or different reaction conditions. Thereby, even when a salt (for example, sodium chloride) is produced as a by-product in the reaction at the first step to inhibit the reaction, it is possible to efficiently carry out the oxidation reaction.

Another example of the oxidation method including the carboxylation is the oxidation method by ozone treatment. By this oxidation reaction, hydroxy groups at least at 2-position and 6-position of a glucopyranose ring are oxidized and the decomposition of the cellulose chains occurs. The ozone treatment is usually carried out by contacting a gas including ozone with the cellulose raw material or the defibrated cellulose fibers.

The lower limit of the ozone concentration in the gas including ozone is preferably 50 $g/m^3$ or more. The upper limit is preferably 250 $g/m^3$ or less, and more preferably 220 $g/m^3$ or less. Therefore, the ozone concentration in the gas including ozone is preferably from 50 to 250 $g/m^3$, and more preferably from 50 to 220 $g/m^3$.

The lower limit of the amount of ozone to be added relative to the cellulose raw material or the defibrated cellulose fibers is preferably 0.1% by mass or more, and more preferably 5% by mass or more, when the solid content of the cellulose raw material or the defibrated cellulose fibers is 100% by mass. The upper limit is preferably 30% by mass or less. Therefore, the amount of ozone to be added relative to the cellulose raw material or the defibrated cellulose fibers is preferably from 0.1 to 30% by mass, and more preferably from 5 to 30% by mass, when the solid content of the cellulose raw material or the defibrated cellulose fibers is 100% by mass.

The lower limit of the ozone treatment temperature is preferably 0° C. or more, and more preferably 20° C. or more. The upper limit is preferably 50° C. or less. Therefore, the ozone treatment temperature is preferably from 0 to 50° C., and more preferably from 20 to 50° C.

The ozone treatment time is not particularly limited, and the lower limit is usually 1 minute or more, and preferably 30 minutes or more. The upper limit is usually 360 minutes or less. Therefore, the ozone treatment time is usually about from 1 to 360 minutes, and preferably about from 30 to 360 minutes.

When the ozone treatment conditions are within these ranges, excessive oxidization and decomposition of the cellulose can be suppressed and the yield of the oxidized cellulose becomes good.

The further additional oxidation treatment with an oxidizing agent may be carried out to the resultant product obtained after the ozone treatment. The oxidizing agent used for the additional oxidation treatment is not particularly limited, and examples thereof include chlorine-based compounds such as chlorine dioxide and sodium chlorite; oxygen, hydrogen peroxide, persulfuric acid, and peracetic acid. The additional oxidation treatment can be carried out, for example, by preparing an oxidizing agent solution by dissolving these oxidizing agents in water or a polar organic solvent such as alcohol, and immersing the cellulose raw material or the defibrated cellulose fibers therein.

The amounts of the carboxy group, the carboxylate group, and the aldehyde group contained in the oxidized cellulose fibers or the oxidized cellulose nanofibers can be adjusted by controlling the oxidation conditions such as the amount of the oxidizing agent to be added and the reaction time.

An example of a method for measuring the amount of the carboxy group will be described below. 60 ml of 0.5% by mass slurry (aqueous dispersion liquid) of the oxidized cellulose fibers or the oxidized cellulose nanofibers is prepared, and 0.1 M hydrochloric acid aqueous solution is added to adjust the pH to 2.5. Thereafter, a 0.05 N sodium hydroxide aqueous solution is added dropwise thereto, and the electric conductivity is measured until the pH reaches 11. The amount of the carboxy group can be calculated by using the following formula based on the amount of sodium hydroxide (a) consumed in the neutralization stage of the weak acid in which the change in the electric conductivity is slow.

Amount of the carboxy group[mmol/g oxidized cellulose fiber or oxidized cellulose nanofiber]=$a$ [ml]×0.05/Mass of oxidized cellulose fiber or oxidized cellulose nanofiber [g]

[1-3-2 Etherification]

Examples of the etherification include etherification by carboxymethylation, etherification by methylation, etherification by ethylation, etherification by cyanoethylation, etherification by hydroxyethylation, etherification by hydroxypropylation, etherification by ethylhydroxyethylation, and etherification by hydroxypropylmethylation. Among them, as an example, a method of carboxymethylation will be described below.

In the case of modifying the cellulose raw material or defibrated cellulose fibers by carboxymethylation, the degree of substitution with carboxymethyl group per anhydrous glucose unit in the resulting carboxymethylated cellulose fibers or cellulose nanofibers is preferably 0.01 or more, more preferably 0.05 or more, and further preferably 0.10 or more. The upper limit is preferably 0.50 or less, more preferably 0.40 or less, and further preferably 0.35 or less. Therefore, the degree of substitution with carboxymethyl group is preferably from 0.01 to 0.50, more preferably from 0.05 to 0.40, and further preferably from 0.10 to 0.35.

The method of carboxymethylation is not particularly limited, and example thereof is a method in which the cellulose raw material or defibrated cellulose fibers as the starting material are mercerized and thereafter etherified. A solvent is usually used in the carboxymethylation reaction. Examples of the solvent include water, alcohols (for example, lower alcohols), and mixed solvents thereof. Examples of the lower alcohol include methanol, ethanol, n-propyl alcohol, isopropyl alcohol, n-butyl alcohol, isobutyl alcohol, and tertiary butyl alcohol. The mixing ratio of the lower alcohol in the mixed solvent is usually 60% by mass or more or 95% by mass or less, and preferably from 60 to 95% by mass. The amount of the solvent is usually 3 times by mass or more relative to the cellulose raw material or the defibrated cellulose fibers. The upper limit is not particularly limited, and is usually 20 times by mass or less. Therefore, the amount of the solvent is preferably from 3 to 20 times by mass.

The mercerization is usually carried out by mixing the starting material and the mercerizing agent. Examples of the mercerizing agent include alkali metal hydroxides such as sodium hydroxide and potassium hydroxide.

The amount of the mercerizing agent to be used is preferably 0.5 times by mol or more, more preferably 1.0 times by mol or more, and further preferably 1.5 times by mol or more per anhydrous glucose residue of the starting material. The upper limit is usually 20 times by mol or less, preferably 10 times by mol or less, and more preferably 5 times by mol or less. Therefore, it is preferably from 0.5 to 20 times by mol, more preferably from 1.0 to 10 times by mol, and further preferably from 1.5 to 5 times by mol.

The reaction temperature of the mercerization is usually 0° C. or more, and preferably 10° C. or more. The upper limit is usually 70° C. or less, and preferably 60° C. or less. Therefore, the reaction temperature is usually from 0 to 70° C., and preferably from 10 to 60° C. The reaction time is usually 15 minutes or more, and preferably 30 minutes or more. The upper limit is usually 8 hours or less, and preferably 7 hours or less. Therefore, it is usually from 15 minutes to 8 hours, and preferably from 30 minutes to 7 hours.

The etherification reaction is usually carried out by adding a carboxymethylating agent to the reaction system after the mercerization. Examples of the carboxymethylating agent include sodium monochloroacetate. Usually, the amount of the carboxymethylating agent to be added is preferably 0.05 times by mol or more, more preferably 0.5 times by mol or more, and further preferably 0.8 times by mol or more per glucose residue of the cellulose raw material or defibrated cellulose fibers. The upper limit is usually 10.0 times by mol or less, preferably 5 times by mol or less, and more preferably 3 times by mol or less. Therefore, it is preferably from 0.05 to 10.0 times by mol, more preferably from 0.5 to 5 times by mol, and further preferably from 0.8 to 3 times by mol. The reaction temperature is usually 30° C. or more, and preferably 40° C. or more. The upper limit is usually 90° C. or less, and preferably 80° C. or less. Therefore, the reaction temperature is usually from 30 to 90° C., and preferably from 40 to 80° C. The reaction time is usually 30 minutes or more, and preferably 1 hour or more. The upper limit is usually 10 hours or less, and preferably 4 hours or less. Therefore, the reaction time is usually from 30 minutes to 10 hours, and preferably from 1 to 4 hours. The reaction solution may be stirred during the carboxymethylation reaction, if needed.

The measurement of the degree of substitution with carboxymethyl group per glucose unit of the carboxymethylated cellulose fibers or carboxymethylated cellulose nanofibers may be carried out, for example, by the following method. Namely, 1) About 2.0 g of the carboxymethylated cellulose (bone-dry) is precisely weighed and placed in a 300 mL stoppered Erlenmeyer flask. 2) Into the flask, 100 mL of a liquid prepared by adding 100 mL of special grade concentrated nitric acid to 1000 mL of methanol is added, and then the resultant mixture is shaken for 3 hours to convert the carboxymethyl cellulose salt (carboxymethylated cellulose salt or CM-modified cellulose salt) into hydrogen type carboxymethylated cellulose (H-CM-modified cellulose). 3) 1.5 to 2.0 g of the hydrogen type carboxymethylated cellulose (bone-dry) is precisely weighed and placed into a 300 mL stoppered Erlenmeyer flask. 4) The hydrogen type carboxymethylated cellulose is wetted with 15 mL of 80% methanol, and then 100 mL of 0.1 N NaOH is added thereto, followed by shaking the resultant mixture for 3 hours at room temperature. 5) Excessive NaOH is back-titrated with 0.1 N $H_2SO_4$ using phenolphthalein as an indicator. 6) The degree of substitution with carboxymethyl group (DS) is calculated in accordance with the following formula:

$$A=[(100 \times F'-(0.1\ N\ H_2SO_4)\ (mL) \times F) \times 0.1]/(\text{bone-dry mass of hydrogen type carboxymethylated cellulose (g)})$$

$$DS=0.162 \times A/(1-0.058 \times A)$$

A: Amount of 1 N NaOH (mL) required for neutralizing 1 g of hydrogen type carboxymethylated cellulose F': Factor of 0.1 N NaOH F: Factor of 0.1 N $H_2SO_4$

[1-3-3. Cationization]

In the case of modifying the cellulose raw material or defibrated cellulose fibers by cationization, the resulting cationized cellulose fibers or cationized cellulose nanofibers may include a cationic group such as ammonium, phosphonium, and sulfonium or a group having the cationic group in the molecule. The cationized cellulose nanofibers preferably include a group having ammonium, and more preferably include a group having quaternary ammonium.

The method of cationization is not particularly limited, and example thereof is a method in which the cellulose raw materials or the defibrated cellulose fibers are reacted with the a cationization agent and a catalyst in the presence of water and/or alcohol. Examples of the cationization agent include glycidyltrimethylammonium chloride, 3-chloro-2-hydroxypropyltrialkylammonium halide (for example, 3-chloro-2-hydroxypropyltrimethylammonium halide), or halohydrin type thereof. By using any of these cationization agents, cationized cellulose fibers or cationized cellulose nanofibers including a group having a quaternary ammonium can be obtained.

Examples of the catalyst include alkali metal hydroxides such as sodium hydroxide and potassium hydroxide. Examples of the alcohol include alcohols having 1 to 4 carbon atoms.

The amount of the cationization agent is preferably 5% by mass or more, and more preferably 10% by mass or more relative to 100% by mass of the cellulose raw material. The upper limit is usually 800% by mass or less, and preferably 500% by mass or less.

The amount of the catalyst is preferably 0.5% by mass or more, and more preferably 1% by mass or more relative to 100% by mass of the cellulose fibers or the defibrated cellulose fibers. The upper limit is usually 7% by mass or less, and preferably 3% by mass or less.

The amount of the alcohol is preferably 50% by mass or more, and more preferably 100% by mass or more relative to 100% by mass of the cellulose fibers or the defibrated cellulose fibers. The upper limit is usually 50000% by mass or less, and preferably 500% by mass or less.

The reaction temperature during the cationization is usually 10° C. or more, and preferably 30° C. or more. The upper limit is usually 90° C. or less, and preferably 80° C. or less.

The reaction time is usually 10 minutes or more, and preferably 30 minutes or more. The upper limit is usually 10 hours or less, and preferably 5 hours or less.

The reaction solution may be stirred during the cationization reaction, if needed.

The degree of substitution with cationic group per glucose unit of the cationized cellulose can be adjusted by controlling the amount of cationization agent to be added and the composition ratio of water and/or alcohol. The degree of substitution with cationic group refers to the number of introduced substituent groups per unit structure (glucopyranose ring) constituting cellulose. In other words, the degree of substitution with cationic group is defined as "a value obtained by dividing the number of moles of the introduced substituent groups by the total number of moles of the hydroxy group in the glucopyranose ring". Pure cellulose has three substitutable hydroxy groups per unit structure (glucopyranose ring) and thus the theoretical maximum value of the degree of substitution with cationic group is 3 (minimum value is 0).

The degree of substitution with cationic group per glucose unit of the cationized cellulose nanofibers is preferably 0.01 or more, more preferably 0.02 or more, and further preferably 0.03 or more. The upper limit is preferably 0.40 or less, more preferably 0.30 or less, and further preferably 0.20 or less. Therefore, it is preferably from 0.01 to 0.40, more preferably from 0.02 to 0.30, and further preferably from 0.03 to 0.20. In the case of introducing the cationic substituent groups into cellulose, the cellulose molecules electrically repel each other. Therefore, it is possible to easily nano-defibrate the cellulose into which the cationic substituent group is introduced. When the degree of substitution with cationic group per glucose unit is 0.01 or more, it is possible to carry out sufficiently nano-defibration. On the other hand, when the degree of substitution with cationic group per glucose unit is 0.40 or less, it is possible to suppress the swelling or dissolution, and thereby to retain the fiber morphology. Accordingly, it is possible to prevent the situation where nanofibers cannot be obtained.

As an example of a method for measuring the degree of substitution with cationic group per glucose unit, it will be described below that the case where 3-chloro-2-hydroxypropyltrimethylammonium chloride is used as a modifying agent. After drying the sample (cationized cellulose), the nitrogen content is measured with a total nitrogen analyzer TN-10 (Mitsubishi Chemical Corporation), and the degree of substitution with cationic group is calculated in accordance with the following formula. The term "degree of substitution with cationic group" here refers to the average value of the number of moles of the substituent groups per 1 mol of anhydrous glucose unit.

$$\text{Degree of substitution with cationic group} = (162 \times N)/(1-116 \times N)$$

N: Nitrogen content

[1-3-4. Esterification]

The method for obtaining esterified cellulose fibers or esterified cellulose nanofibers by esterifying the cellulose raw material or the defibrated cellulose fibers is not particularly limited, and, example thereof is a method in which the cellulose raw material or the defibrated cellulose fibers are reacted with a compound A. The compound A will be described below.

Examples of the method for reacting the cellulose raw material or the defibrated cellulose fibers with the compound A include a method for mixing the powder or the aqueous solution of the compound A to the cellulose raw material or the defibrated cellulose fibers, and a method for adding the aqueous solution of the compound A to the slurry of the cellulose raw material or the defibrated cellulose fibers. Among them, the method for mixing the aqueous solution of the compound A to the cellulose raw material, the defibrated cellulose fibers, or slurry thereof is preferable because the uniformity of the reaction is enhanced and the esterification efficiency is improved.

Examples of the compound A include phosphoric acid-based compound (for example, phosphoric acid and polyphosphoric acid), phosphorous acid, phosphonic acid, polyphosphonic acid, and esters thereof. The compound A may be in the form of a salt. Among them, the phosphoric acid-based compounds are preferable because the compounds are low in cost as well as easy to handle, and allow defibration efficiency to be improved by introducing phosphate groups to the cellulose of the cellulose raw material (for example, pulp fibers). The phosphoric acid-based compound may be a compound having a phosphate group, and examples thereof include phosphoric acid, sodium dihydrogen phosphate, disodium hydrogen phosphate, trisodium phosphate, sodium pyrophosphate, sodium metaphosphate, potassium dihydrogen phosphate, dipotassium hydrogen phosphate, tripotassium phosphate, potassium pyrophosphate, potassium metaphosphate, ammonium dihydrogen phosphate, diammonium hydrogen phosphate, triammonium hydrogen phosphate, ammonium pyrophosphate, and ammonium metaphosphate. The phosphoric acid-based compound to be used may be used singly or in combination of two or more compounds. Among them, the compounds are preferably the phosphoric acid, the sodium salts of phosphoric acid, the potassium salts of phosphoric acid, and the ammonium salts of phosphoric acid, more preferably the sodium salts of phosphoric acid, and further preferably sodium dihydrogen phosphate and disodium hydrogen phosphate from the viewpoints that the efficiency of introducing the phosphate group is high, and that it is easy to defibrate these compounds in the defibration process described below as well as apply these compounds in industry. In addition, it is preferably to use the aqueous solution of the phosphoric acid-based compound in esterification because uniformity of the reaction is enhanced and the efficiency of introducing the phosphate group becomes high. The pH of the aqueous solution of the phosphoric acid-based compound is preferably 7 or less because the efficiency of introducing the phosphate group becomes high. The pH is more preferably from 3 to 7 from the viewpoint of suppressing the hydrolysis of pulp fibers.

As examples of the method of esterification, the following method is described. Phosphate groups are introduced to the cellulose by adding the compound A into the suspension of the cellulose raw material or the defibrated cellulose fibers (for example, a solid content concentration from 0.1 to 10% by mass) while stirring. When the cellulose raw material or the defibrated cellulose fibers are determined to be 100 parts by mass, the amount of the compound A to be added is preferably 0.2 part by mass or more, and more preferably 1 part by mass or more as the amount of phosphorus element in the case where the compound A is a phosphoric acid-based compound. Thereby, it is possible to further improve the yield of the esterified cellulose fibers or the esterified cellulose nanofibers. The upper limit is preferably 500 parts by mass or less, and more preferably 400 parts by mass or less. Thereby, it is possible to efficiently obtain the yield corresponding to the amount of the compound A to be used. Accordingly, it is preferably from 0.2 to 500 parts by mass, and more preferably from 1 to 400 parts by mass.

When the cellulose materials or the defibrated cellulose fibers are reacted with the compound A, a compound B may be further added to the reaction system. Example of the method for adding the compound B to the reaction system is a method in which the compound B is added to the slurry of the cellulose raw material or the defibrated cellulose fibers, the aqueous solution of the compound A, or the slurry of the cellulose raw material or the defibrated cellulose fibers and the compound A.

The compound B is not particularly limited. The compound B is preferably exhibits basicity, and more preferably nitrogen-containing compounds exhibiting basicity. The term "exhibiting basicity" usually means that the aqueous solution of the compound B exhibits color of pink to red in the presence of phenolphthalein indicator and/or that the pH of the aqueous solution of the compound B is more than 7. The nitrogen-containing compounds exhibiting basicity are not particularly limited as long as they show the effects of the present invention, and preferably compounds having an amino group. Examples of the compounds having an amino group include urea, methylamine, ethylamine, trimethylamine, triethylamine, monoethanolamine, diethanolamine, triethanolamine, pyridine, ethylenediamine, and hexamethylenediamine. Among them, urea is preferable from the viewpoint of low cost and easy handling. The amount of the compound B to be added is preferably from 2 to 1000 parts by mass, and more preferably from 100 to 700 parts by mass. The reaction temperature is preferably from 0 to 95° C., and more preferably from 30 to 90° C. The reaction time is not particularly limited, and is usually about from 1 to 600 minutes, and preferably from 30 to 480 minutes. When the conditions of the esterification reaction are within any of these ranges, it is possible to prevent the cellulose from being easily dissolved due to the excessive esterification thereof, and then, to improve the yield of the phosphate-esterified cellulose.

After the compound A is reacted with the cellulose raw material or the defibrated cellulose fibers, suspension of esterified cellulose fibers or esterified cellulose nanofibers is usually obtained. The suspension of the esterified cellulose fibers or the esterified cellulose nanofibers is dehydrated, if needed. It is preferably to carry out the heating treatment after the dehydration. Thereby, it is possible to suppress the hydrolysis of the cellulose raw material or the defibrated cellulose fibers. The heating temperature is preferably from 100 to 170° C. More preferably, the heating treatment is carried out at 130° C. or less (further preferably, 110° C. or less) while water is included at the time of heating treatment, and then carried out from 100 to 170° C. after water is removed.

In the phosphate-esterified cellulose, phosphate substituent groups are introduced to the cellulose, and the celluloses electrically repel each other. Therefore, it is possible to easily defibrate the phosphate-esterified cellulose fibers to the cellulose nanofibers (the defibration carried out until the cellulose nanofibers are formed is also referred to as nano-defibration). The degree of substitution with the phosphate group per glucose unit of the phosphate-esterified cellulose fibers is preferably 0.001 or more. Thereby, it can achieve the sufficient defibration (for example, nano-defibration). The upper limit is preferably 0.40 or less. Thereby, it is possible to suppress the swelling or dissolution of the phosphate-esterified cellulose fibers and generation of the situation where cellulose nanofibers cannot be obtained. Therefore, it is preferably from 0.001 to 0.40. Moreover, the degree of substitution with the phosphate group per glucose unit of the cellulose nanofibers modified by phosphate esterification (phosphate-esterified cellulose nanofibers) is preferably 0.001 or more. The upper limit is preferably 0.40 or less. Therefore, the degree of substitution with the phosphate group per glucose unit of the phosphate-esterified cellulose nanofibers is preferably from 0.001 to 0.40.

It is preferably to subject the phosphate-esterified cellulose fibers to washing treatment such as washing with cold water after boiling. Thereby, the defibration can be carried out effectively.

[1-4 Defibration]

Defibration may be carried out before subjecting the cellulose raw material to the modification treatment, or may be carried out to the chemically modified cellulose fibers (for example, oxidized cellulose fibers, carboxymethylated cellulose fibers, cationized cellulose fibers, and esterified cellulose fibers (phosphate-esterified cellulose fibers)) after subjecting the cellulose raw material to the modification treatment. Since the energy required for defibration is reduced by modification, it is preferably to carry out the defibration after subjecting the cellulose raw material to the modification treatment.

The defibration may be carried out at once, or may be carried out a plurality of times. In the case where the defibration is carried out a plurality of times, each defibration can be carried out anytime.

An apparatus used for defibration is not particularly limited, and examples thereof include a high-speed rotation type apparatus, a colloid mill type apparatus, a high pressure type apparatus, a roll mill type apparatus, and an ultrasonic type apparatus. A high pressure or ultrahigh pressure homogenizer is preferable, and a wet type high pressure or ultrahigh pressure homogenizer is more preferable. These apparatuses are preferable because they are capable of applying strong shear force to the cellulose raw material or the chemically modified cellulose fibers (usually an aqueous dispersion).

In order to efficiently defibrate, the pressure applied to the cellulose raw material or the chemically modified cellulose fibers (usually the aqueous dispersion) is preferably 50 MPa or more, more preferably 100 MPa or more, and further preferably 140 MPa or more. The apparatus is preferably a wet type high pressure or ultrahigh pressure homogenizer because they can apply the above pressure as well as strong shear force to the cellulose raw material or the chemically modified cellulose fibers (usually the aqueous dispersion).

Moreover, a preliminary treatment may be carried out prior to the defibration (preferably defibration with a high pressure homogenizer), or the dispersion treatment before the defibration carried out when necessary, if needed. Examples of the preliminary treatment include mixing, stirring, emulsification, and dispersion. The preliminary treatment may be carried out using a known device (for example, a high speed shear mixer).

When the defibration is carried out to the dispersion (usually an aqueous dispersion) of the cellulose raw material or the chemically modified cellulose fibers, the lower limit of the solid content as the cellulose raw material or the chemically modified cellulose fibers in the dispersion is usually 0.1% by mass or more, preferably 0.2% by mass or more, and more preferably 0.3% by mass or more. Thereby, it becomes the appropriate liquid amount relative to the amount of the cellulose raw material or chemically modified cellulose fiber, which is effective. The upper limit is usually 10% by mass or less, and preferably 6% by mass or less. Thereby, it is possible to retain the flowability.

[1-5. Form]

The form of the cellulose nanofibers is not particularly limited, and examples thereof include the dispersion liquid of the cellulose nanofibers, the dried solid of the dispersion liquid, the moist solid of the dispersion liquid, the mixture liquid of the cellulose nanofibers and a water-soluble polymer, the dried solid of the mixture liquid, the moist solid of the mixture liquid, and other known forms of the cellulose nanofibers. Here, the moist solid is a solid in an intermediate mode between the dispersion liquid or mixture liquid and the dried solid.

The dried solid and the wet solid of the dispersion liquid of the cellulose nanofiber or the mixture liquid of the cellulose nanofiber and the water-soluble polymer may be prepared by dehydrating and/or drying the dispersion liquid or the mixture liquid.

[2. Other Optional Components that May be Included in Stock Solution]

The stock solution may optionally include other components besides the cellulose nanofibers. Other components are not particularly limited, and examples thereof include a fatty acid soap, a surfactant, a liquid dispersion medium, an inorganic compound (for example, a metal oxide, a metal, an inorganic salt, and a silica-based compound), an organic compound except for the cellulose nanofibers (for example, oils, gums, latexes, and water-soluble polymers), a moisturizer, an ultraviolet ray shielding agent, and an antibacterial-antiseptic agent.

[Fatty Acid Soap]

The foamable aerosol composition of the present invention may include the fatty acid soap in the stock solution. The fatty acid soap may be included in the stock solution by adding an alkali fatty acid to the stock solution, or the fatty acid soap may be included in the stock solution by adding a fatty acid and an alkaline agent to the stock solution.

The fatty acid constituting the fatty acid soap is not particularly limited, and may be a known fatty acid or one usually used in cosmetics. Examples of the fatty acid include saturated linear fatty acids such as lauric acid, myristic acid, palmitic acid, stearic acid, and behenic acid; and unsaturated linear fatty acids such as oleic acid, linoleic acid, and linolenic acid. The fatty acid constituting the fatty acid soap may be used singly or in combination of two or more fatty acids. The amount of the fatty acid to be added is preferably in the range from 1 to 10% by mass of the stock solution. When it is 1% by mass or more, it tends to obtain the ejected substance more excellent foamability, and when it is 10% by mass or less, good stability is achieved such that precipitation is hardly occur in the stock solution.

The alkali agent constituting the fatty acid soap is not particularly limited, and may be a known alkaline agent or ones usually used in cosmetics. Examples of the alkaline agent include sodium hydroxide, potassium hydroxide, ammonium hydroxide, monoethanolamine, diethanolamine, triethanolamine, and aminomethylpropanol. The amount of the alkaline agent to be added is preferably in the range from 0.1% to 5% by mass of the stock solution.

[Surfactant]

The foamable aerosol composition of the present invention may include the surfactant in the stock solution, and preferably includes the surfactant. By including the surfactant, the better foam may be formed with expansion of the propellant after the foamable aerosol composition is ejected from the container. The kinds of the surfactant are not particularly limited, and any known ones may be used. Examples of the surfactant include a nonionic surfactant, an anionic surfactant, a cationic surfactant, and an amphoteric surfactant. Among them, the nonionic surfactant is preferable from the viewpoint of low irritation to skin.

The surfactant may be included singly in the stock solution or may be included in the stock solution in combination of two or more surfactants.

Examples of the nonionic surfactant include a propylene glycol fatty acid ester, a glycerin fatty acid ester, a polyglycerin fatty acid ester, a sorbitan fatty acid ester, a sucrose fatty acid ester, a polyoxyethylene glycerin fatty acid ester, a polyoxyethylene sorbitan fatty acid ester, a polyoxyethylene sorbitol fatty acid ester, a polyethylene glycol fatty acid ester, polyoxyethylene castor oil, polyoxyethylene hydrogenated castor oil, a polyoxyethylene alkyl ether, a polyoxyethylene alkyl phenyl ether, polyoxyethylene phytostanol ether, and a polyether-modified silicone. Among them, polyoxyethylene phytostanol ether is particularly preferable from the viewpoint that foamability and a foaming property are good.

Examples of the anionic surfactant include a polyoxyethylene alkyl ether carboxylic acid salt, a N-acylsarcosine salt, a N-acylglutamic acid salt, a dialkyl sulfosuccinic acid salt, an alkane sulfonic acid salt, an α-olefin sulfonic acid salt, a linear alkylbenzene sulfonic acid salt, a branched alkylbenzene sulfonic acid salt, a naphthalene sulfonic acid salt-formaldehyde condensate, an alkyl naphthalene sulfonic acid salt, a N-methyl-N-acyl taurine salt, an alkylsulfuric acid salt, a polyoxyethylene alkyl ether sulfuric acid salt, an alkylphosphorus acid salt, and a polyoxyethylene alkyl phenyl ether phosphate salt.

Examples of the cationic surfactant include an alkyltrimethylammonium chloride, a dialkyldimethylammonium chloride, and an alkylbenzalkonium chloride.

Examples of the amphoteric surfactant include an alkyl betaine, a fatty acid amidopropyl betaine, a 2-alkyl-N- carboxymethyl-N-hydroxyethyl imidazolinium betaine, and an alkyl diethylenetriaminoacetic acid.

The amount of the surfactant to be added is preferably in the range from 0.05 to 10% by mass of the total stock solution. When it is 0.05% by mass or more, the foaming property and foam retention is sufficient. When it is 10% by mass or less, the retention time of the foam is appropriate. Consequently, the foamable aerosol composition of the present invention can be suitably used for various applications.

[Liquid Dispersion Medium]

The foamable aerosol composition in the present invention may include one or more liquid dispersion media for dispersing each component in the stock solution, if needed. The liquid dispersion medium is not particularly limited, and examples thereof include water and a water-soluble organic solvent. The water-soluble organic solvent is not particularly limited, and examples thereof include alkyl alcohols having 1 to 4 carbon atoms such as methanol, ethanol, n-propyl alcohol, iso-propyl alcohol, n-butyl alcohol, sec-butyl alcohol, and tert-butyl alcohol; amides such as dimethylformamide and dimethylacetamide; ketones or ketoalcohols such as acetone and diacetone alcohol; ethers such as tetrahydrofuran and dioxane; and carbitols. The liquid dispersion medium may be included singly in the stock solution, or may be included in the stock solution as a mixture medium of two or more liquid dispersion media. The liquid dispersion medium is preferably water.

[Inorganic Compound]

The foamable aerosol composition in the present invention may include one or more inorganic compounds such as a metal oxide, a metal, an inorganic salt, and a silica-based compound in the stock solution, if needed. The inorganic compound may be included singly in the stock solution, or may be included in the stock solution in combination of two or more inorganic compounds.

The metal oxide is not particularly limited, and examples thereof include titanium dioxide, alumina, zinc dioxide, iron oxide red, and yellow iron oxide.

The metal is not particularly limited, and examples thereof include gold, silver, copper, aluminum, magnesium, zinc, and iron.

The inorganic salt is not particularly limited, and examples thereof include sodium chloride, calcium chloride, magnesium chloride, ammonium sulfate, and calcium phosphate.

The silica-based compound is not particularly limited, and examples thereof include zeolite, montmorillonite, asbestos, smectite, mica, fumed silica, and colloidal silica.

[Organic Compound]

The foamable aerosol composition in the present invention may include one or more organic compounds such as oils, gums, latexes, and water-soluble polymers in the stock solution except for the cellulose nanofibers, if needed. The organic compound may be included singly in the stock solution, or may be included in the stock solution in combination of two or more organic compounds.

The oils are not particularly limited, and examples thereof include natural animal and plant fat and oil such as *jojoba* oil, *Macadamia* nut oil, *avocado* oil, evening primrose oil, mink oil, rapeseed oil, castor oil, sunflower oil, corn oil, *Cacao* oil, coconut oil, rice bran oil, olive oil, almond oil, *sesame* oil, safflower oil, soybean oil, *Camellia* oil, persic oil, cottonseed oil, Japanese wax, palm oil, palm kernel oil, egg yolk oil, lanolin, and squalene; hydrocarbons such as synthetic triglyceride, squalane, liquid paraffin, petrolatum, ceresin, microcrystalline wax, and isoparaffin; waxes such as caranuba wax, paraffin wax, whale wax, beeswax, candelilla wax, and lanolin: higher alcohols such as cetanol, stearyl alcohol, lauryl alcohol, cetostearyl alcohol (cetearyl alcohol), oleyl alcohol, behenyl alcohol, lanolin alcohol, hydrogenated lanolin alcohol, hexyldecanol, and octyldodecanol; higher fatty acids such as lauric acid, myristic acid, palmitic acid, stearic acid, behenic acid, isostearic acid, oleic acid, linolenic acid, linoleic acid, oxystearic acid, undecylenic acid, a lanolin fatty acid, a hard lanolin fatty acid, and a soft lanolin fatty acid: cholesterol and derivatives thereof such as cholesteryl-octyldodecyl-behenyl; esters such as isopropyl myristate, isopropyl palmitate, isopropyl stearate, glycerol 2-ethylhexanoate, and butyl stearate; polar oils such as diethylene glycol monopropyl ether, polyoxyethylene polyoxypropylene pentaerythritol ether, poly oxypropylene butyl ether, and ethyl linoleate: and more specifically silicone resins such as an amino-modified silicone, an epoxy-modified silicone, a carboxy-modified silicone, a carbinol-modified silicone, a methacryl-modified silicone, a mercapto-modified silicone, a phenol-modified silicone, a reactive silicone at one terminal, a hetero-functional group-modified silicone, a polyether-modified silicone, a methylstyryl-modified silicone, an alkyl-modified silicone, a higher fatty acid ester-modified silicone, a specific-modified hydrophilic silicone, a higher alkoxy-modified silicone, a higher fatty acid-containing silicone, a fluorine-modified silicone, and the like; and silicones including various derivatives such as methylphenylpolysiloxane, methylpolysiloxane, octamethylcyclotetrasiloxane, decamethylcyclopentasiloxane, dodecamethylcyclohexanesiloxane, methylcyclopolysiloxane, octamethyltrisiloxane, decamethyltetrasiloxane, a polyoxyethylene-methylpolysiloxane copolymer, a polyoxypropylene-methylpolysiloxane copolymer, a poly(oxyethylene-oxypropylene)methylpolysiloxane copolymer, methylhydrogenpolysiloxane, tetrahydrotetramethylcyclotetrasiloxane, stearoxymethylpolysiloxane, cetoxymethylpolysiloxane, methylpolysiloxane emulsion, highly polymerized methylpolysiloxane, trimethylsiloxy silicic acid, crosslinked methylpolysiloxane, and crosslinked methylphenylpolysiloxane. Among them, cetostearyl alcohol (cetearyl alcohol), stearic acid, behenic acid, and behenyl alcohol are preferable from the viewpoints of foam elasticity and foam retention.

The gums are not particularly limited, and examples thereof include gum arabic, xanthan gum, guar gum, locust bean gum, quince seed, and carrageenan. Among them, xanthan gum is preferred from the viewpoints of foam elasticity and foam retention.

The latexes are not particularly limited, and examples thereof include styrene-butadiene copolymer latexes and acrylic latexes.

The water-soluble polymers are not particularly limited, and examples thereof include polyvinyl alcohol, cationized cellulose, a carboxyvinyl polymer, polyvinyl pyrrolidone, a polyvinyl pyrrolidone/vinyl acetate copolymer, polyacrylic acid, polyacrylamide, alginic acid, polydextrose, carboxymethyl cellulose, and hydroxyethyl cellulose. Carboxymethyl cellulose is preferable.

[3. Active Component in Specific Application that May be Included in Stock Solution]

The foamable aerosol composition in the present invention may include an active component in specific applications in addition to the above components in the stock solution. When the foamable aerosol composition is, for example, used in cosmetics, the foamable aerosol composition may include one or more moisturizers, ultraviolet ray shielding agents, antibacterial-antiseptic agent, and the like.

The moisturizer is not particularly limited, and examples thereof the moisturizer include polyvalent alcohols such as maltitol, sorbitol, glycerin, diglycerin, propylene glycol, butylene glycol, polyethylene glycol, and glycol; organic acids and salts thereof such as sodium pyrrolidonecarboxylate, sodium lactate, and citric acid; hyaluronic acid and salts thereof such as sodium hyaluronate; fermented metabolic products such as yeast as well as yeast extract hydrolyzate, yeast culture liquid, and lactic acid bacteria culture liquid; water-soluble proteins such as collagen, elastin, keratin, and sericin; peptides and salts thereof such as collagen hydrolyzate, casein hydrolyzate, silk hydrolyzate, and sodium polyaspartate; saccharides/polysaccharides and derivatives thereof such as trehalose, xylobiose, maltose, sucrose, glucose, and vegetable mucopolysaccharide; glycosaminoglycans and salts thereof such as water-soluble chitin, chitosan, pectin, and chondroitin sulfuric acid and a salt thereof; amino acids compounds such as glycine, serine, threonine, alanine, aspartic acid, tyrosine, valine, leucine, arginine, glutamine, and proline; glico-amino acid compounds such as aminocarbonyl reactants; plant extracted liquids of aloe, malonnier, and the like; trimethylglycine, urea, uric acid, ammonia, lecithin, lanolin, squalane, squalene, glucosamine, creatinine, and nucleic acid related substances such as DNA and RNA. Among them, glycerin, diglycerin, citric acid and a salt thereof, polyethylene glycol, and butylene glycol are preferable from the viewpoints of a foam-forming property and moisture retention. The moisturizer may be included singly in the stock solution, or may be included in the stock solution in combination of two or more moisturizers.

The ultraviolet ray shielding agent is not particularly limited, and examples thereof the ultraviolet ray shielding agent include p-aminobenzoic acid and derivatives thereof; homomethyl-N-acetyl-anthranilate; butylmethoxybenzoylmethane; p-methoxycinnamic acid derivatives such as glyceryl di-p-methoxycinnamate-mono-2-ethylhexanoate and octyl cinnamate; salicylic acid derivatives such as amyl salicylate; benzophenone derivatives such as 2,4-dihydroxybenzophenone; ethylhexyl dimethoxybenzylidenedioximidazolinepropionate; liquid lanolin acetate; root extract of Scutellaria baicalensis; and trianilino-p-carboethylhexyloxy-triazine. The ultraviolet ray shielding agent may be included singly in the stock solution, or may be included in the stock solution in combination of two or more ultraviolet ray shielding agents.

The antibacterial-antiseptic agent is not particularly limited, and examples thereof include benzoic acid and salts thereof, salicylic acid and salts thereof, sorbic acid and salts thereof, a paraoxybenzoic acid alkyl ester (ethylparaben, butylparaben, and the like) and salts thereof, dehydroacetic acid and salts thereof, parachloromethacresol, hexachlorophene, boric acid, resorcin, tribromsalane, orthophenylphenol, chlorhexidine gluconate, thiram, photosensitizer 201, phenoxyethanol, benzalkonium chloride, benzethonium chloride, halocarban, chlorhexidine chloride, trichlorocarbanide, tocopherol acetate, zinc pyrithione, hinokitiol, phenol, isopropylmethylphenol, 2,4,4-trichloro-2-hydroxyphenol, and hexachlorophene. Among them, phenoxyethanol is preferable. The antibacterial-antiseptic agent may be included singly in the stock solution, or may be included in the stock solution in combination of two or more antibacterial-antiseptic agent.

<Method for Producing Foamable Aerosol Composition>

The method for producing the foamable aerosol composition of the present invention is not particularly limited, and it is possible to produce the foamable aerosol composition by conventionally known methods. For example, it is possible to obtain the foamable aerosol composition of the present invention by mixing each component included in the stock solution using a conventionally known method (for example, mixing using a homomixer or the like) to prepare the stock solution, filling the stock solution in an aerosol container (for example, a can) having pressure tightness, equipping a valve for ejection, and further filling the propellant to pressurize inside the container. During the production, the stock solution may be heated or cooled, if needed.

<<B>> Kit of the Present Invention

The present invention provides a kit including the aerosol container and the foamable aerosol composition filled in the aerosol container.

As to the foamable aerosol composition included in the kit of the present invention, it has been already described in above section <<A>>.

The aerosol container is not particularly limited, and may be a known aerosol container, provided that the aerosol container has pressure resistance depending on the foamable aerosol composition to be included therein.

The kit of the present invention preferably includes a valve.

The method for producing the kit of the present invention is not particularly limited, and it can be produced by conventionally known methods.

The internal pressure of the aerosol container in the kit of the present invention is not particularly limited, and is preferably adjusted to be from 0.3 to 1.5 MPa at 25° C.

The foamable aerosol composition of the present invention can be used as household products such as deodorants, fragrances, cleaners, and waxes, personal products such as cosmetics and medicines, paint products, insecticidal products, industrial products such as metal flaw detection agents and antirust agents, and automobileproducts. Among them, it is suitably used for cosmetics, and particularly preferably used for facial treatment mask (pack cosmetic). Namely, the present invention provides a foamable aerosol composition serving as the facial treatment mask.

EXAMPLES

Hereinafter, the present invention will be described in further detail with reference to Examples. The present invention, however, is not limited thereto.

Example 1

[Production of Oxidized Cellulose Nanofiber]

5.00 g of bleached unbeaten kraft pulp (bone-dry) derived from softwood (a degree of whiteness 85%) was added to 500 ml of an aqueous solution in which 39 mg (0.05 mmol relative to 1 g of the bone-dry cellulose) of TEMPO (manufactured by Sigma Aldrich Co. LLC.) and 514 mg of sodium bromide (1.0 mmol relative to 1 g of the bone-dry cellulose) were dissolved, and the resultant mixture was stirred until the pulp was uniformly dispersed. An aqueous solution of sodium hypochlorite was added to the reaction system so that sodium hypochlorite was 5.5 mmol/g relative to 1 g of the bone-dry cellulose, and oxidation reaction was started at room temperature. During the reaction, the pH in the system decreased and thus 3M sodium hydroxide aqueous solution was added sequentially to adjust the pH at 10. The reaction was finished when sodium hypochlorite was consumed and the pH in the system did not change.

The mixture after the reaction was filtered with a glass filter to separate the pulp, and the pulp was sufficiently washed with water to obtain an oxidized pulp (carboxylated cellulose). The yield of the pulp at this time was 90%, the time required for the oxidation reaction was 90 minutes, and the amount of carboxy group was 1.6 mmol/g. The solid content of this pulp was adjusted with water to 1.0% (w/w), and the resultant mixture was treated with an ultrahigh pressure homogenizer (20° C., 150 MPa) at three times to obtain the aqueous dispersion liquid of oxidized cellulose nanofibers. The oxidized cellulose nanofibers had an average fiber diameter of 3 nm and an aspect ratio of 250.

[Production of Foamable Aerosol Product (Kit)]

Assuming a facial treatment mask, stock solution materials according to the formulation listed in Table 1 were stirred for about 30 minutes at a rotation speed of 400 rpm using a propeller stirrer (manufactured by Shinto Scientific Co., Ltd., model name: BLh600) to obtain a stock solution. This stock solution was filled in an aerosol container, and liquefied natural gas (LPG) was further filled as a propellant in the aerosol container at a ratio of stock solution: LPG=96% by mass %:4% by mass. Carbon dioxide gas was further filled therein so that the pressure reached to 0.5 MPa, and the ejection nozzle part being foam ejection type in the ejection form was equipped therewith to produce the foamable aerosol product (kit) containing the foamable aerosol composition serving as a facial treatment mask. As to the obtained foamable aerosol product, the following evaluation were executed in accordance with the following methods: an ejection state, for evaluating the suitability for the foamable aerosol composition; and foam state, elasticity of foam, ease of foam-spreading, and adsorptive ability to the skin, for evaluating the suitability for the facial treatment mask.

[Ejection State]

The composition was ejected on a horizontal glass plate for 5 seconds, and the ejection state was visually observed. The ejection state was evaluated in accordance with the following criteria.

x: The composition is not discharged from the nozzle and cannot be ejected.

Δ: The composition is ejected from the nozzle but the ejection is discontinuous.

○: The composition is continuously ejected from the nozzle.

[Foam State]

The foamable aerosol composition was ejected on a horizontal glass plate for 5 seconds, and the bubble size in the foam was visually observed. The foam state was sensuously evaluated in accordance with the following criteria.

x: The composition is ejected in a liquid form instead of a foam form.

Δ: The foam are large size or non-uniform.

○: The foam are dense and uniform.

[Elasticity of Foam]

The foamable aerosol composition ejected on a horizontal glass plate for 5 seconds was pushed with a finger. The elasticity of the foam was sensuously evaluated in accordance with the following criteria.

x: The foam has little elasticity

Δ: The foam has elasticity but the elasticity is insufficient

○: The foam has sufficient resilience

[Ease of Foam-Spreading]

The foamable aerosol composition ejected on a palm for 5 seconds was spread on a skin. The ease of foam-spreading was sensuously evaluated in accordance with the following criteria.

x: The foam is difficult to spread

Δ: The foam spreads but the degree of spread is insufficient.

○: The foam remarkably spreads.

[Adsorptive Ability to Object (Skin)]

The foamable aerosol composition ejected on a palm for 5 seconds was spread on a skin. The adsorbability to skin was sensuously evaluated in accordance with the following criteria.

x: The foam is hardly adsorbed

Δ: The foam is slightly adsorbed

○: The foam is adsorbed

◎: The foam is remarkably adsorbed

Example 2

Example 2 was carried out in the same manner as Example 1 except that the amount of the aqueous dispersion liquid of the oxidized cellulose nanofibers to be added in Example 1 was changed as listed in Table 1.

Example 3

Example 3 was carried out in the same manner as Example 1 except that the aqueous dispersion liquid of the oxidized cellulose nanofibers used in Example 1 was changed to the aqueous dispersion liquid of carboxymethylated cellulose nanofibers produced by the following method and it was added as listed in Table 1.

[Production of Carboxymethylated Cellulose Nanofiber]

Into a stirrer capable of mixing pulp, 200 g as dry mass of a pulp (NBKP (softwood bleached kraft pulp), manufactured by Nippon Paper Industries Co., Ltd.) and 111 g as dry mass of sodium hydroxide (2.25 times by mol per anhydrous glucose residue of the starting material) were added, and water was added so that the pulp solid content was 20% (w/v). Thereafter, after the resultant mixture was stirred at 30° C. for 30 minutes, 216 g of sodium monochloroacetate (in terms of active component, 1.5 times by mol per glucose residue of the pulp) was added. After the resultant mixture was stirred for 30 minutes, the temperature was raised to 70° C. and the mixture was stirred for 1 hour. Thereafter, the reaction product was taken out, neutralized, and washed to obtain a carboxymethylated pulp having a degree of substitution with carboxymethyl group per glucose unit of 0.25. This product was diluted with water so that the solid content was 1% (w/w), and the resultant was defibrated by treating five times with a high pressure homogenizer at 20° C. and at a pressure of 150 MPa to obtain carboxymethylated cellulose nanofibers. The average fiber diameter was 15 nm and the aspect ratio was 50.

Example 4

Example 4 was carried out in the same manner as Example 1 except that the aqueous dispersion liquid of the oxidized cellulose nanofibers used in Example 1 was changed to the aqueous dispersion liquid of carboxymethylated cellulose nanofiber-containing composition (dried solid) produced by the following method and it was added as listed in Table 1.

[Production of Aqueous Dispersion Liquid of Carboxymethylated Cellulose Nanofiber-Containing Composition (Dried Solid)]

Carboxymethylated cellulose nanofibers (average fiber diameter: 15 nm, aspect ratio: 50) produced by the same method as Example 3 were adjusted to an aqueous suspension liquid having a solid content of 0.7% by mass. To the adjusted aqueous suspension liquid, 40% by mass of carboxymethyl cellulose (trade name: F350HC-4, supplied from Nippon Paper Industries Co., Ltd.) relative to the carboxymethylated cellulose nanofibers was added and the resultant mixture was stirred with a mixer (TK HOMO-MIXER, manufactured by PRIMIX Corporation) at 12,000 rpm for 60 minutes. To the stirred aqueous suspension liquid, a 0.5% sodium hydroxide aqueous solution was added to adjust a pH to 9. Thereafter, the resultant was dried at a steam pressure of 0.5 MPa. G, and a drum rotation number of 2 rpm using a drum dryer (D0303, manufactured by KATSURAGI INDUSTRY CO., LTD.) to obtain a carboxymethylated cellulose nanofiber-containing composition (dried solid) having a water content of 5% by mass. This dried solid was diluted with water so that the solid content was 1% (w/w), and the resultant was stirred at 6,000 rpm for 60 minutes using a mixer (TK Homomixer, manufactured by Primix Corporation) to obtain an aqueous dispersion liquid of the carboxymethylated cellulose nanofiber-containing composition (dried solid). The 1% by mass aqueous dispersion liquid of the carboxymethylated cellulose nanofiber-containing composition (dried solid) includes 0.7% by mass of the carboxymethylated cellulose nanofiber and 0.3% by mass of the carboxymethyl cellulose.

Comparative Example 1

Comparative Example 1 was carried out in the same manner as Example 1 except that the oxidized cellulose nanofibers used in Example 1 were not added and the compound was formed in accordance with the formulation listed in Table 1.

Comparative Example 2

Comparative Example 2 was carried out in the same manner as Example 1 except that the oxidized cellulose nanofibers used in Example 1 were not added and xanthan gum (product name: Echo Gum F, manufactured by DSP GOKYO FOOD & CHEMICAL Co., Ltd.) was added in accordance with the formulation listed in Table 1.

Comparative Example 3

Comparative Example 3 was carried out in the same manner as Example 1 except that the oxidized cellulose nanofibers used in Example 1 were not added and hydroxyethyl cellulose (product name: HEC SE550, manufactured by Daicel FineChem Ltd.) was added in accordance with the formulation listed in Table 1.

Comparative Example 4

Comparative Example 4 was carried out in the same manner as Example 1 except that the oxidized cellulose nanofibers used in Example 1 were not added and hydroxyethyl cellulose (product name: HEC SE550, manufactured by Daicel FineChem Ltd.) was added in accordance with the formulation listed in Table 1.

TABLE 1

|  | Ex. 1 | Ex. 2 | Ex. 3 | Ex. 4 | Comp. Ex. 1 | Comp. Ex. 2 | Comp. Ex. 3 | Comp. Ex. 4 |
| --- | --- | --- | --- | --- | --- | --- | --- | --- |
| Water | 68.95 | 69.45 | 69.45 | 69.45 | 69.95 | 69.75 | 69.85 | 69.94 |
| Glycerin | 6.00 | 6.00 | 6.00 | 6.00 | 6.00 | 6.00 | 6.00 | 6.00 |
| Diglycerin | 4.20 | 4.20 | 4.20 | 4.20 | 4.20 | 4.20 | 4.20 | 4.20 |
| Butylene glycol | 4.20 | 4.20 | 4.20 | 4.20 | 4.20 | 4.20 | 4.20 | 4.20 |
| Potassium hydroxide | 0.35 | 0.35 | 0.35 | 0.35 | 0.35 | 0.35 | 0.35 | 0.35 |
| Polyoxyethylene phytostanol | 4.00 | 4.00 | 4.00 | 4.00 | 4.00 | 4.00 | 4.00 | 4.00 |
| Cetearyl alcohol | 4.00 | 4.00 | 4.00 | 4.00 | 4.00 | 4.00 | 4.00 | 4.00 |
| Behenic acid | 2.50 | 2.50 | 2.50 | 2.50 | 2.50 | 2.50 | 2.50 | 2.50 |
| Stearic acid | 1.80 | 1.80 | 1.80 | 1.80 | 1.80 | 1.80 | 1.80 | 1.80 |
| Behenyl alcohol | 1.80 | 1.80 | 1.80 | 1.80 | 1.80 | 1.80 | 1.80 | 1.80 |
| Phenoxyethanol | 0.60 | 0.60 | 0.60 | 0.60 | 0.60 | 0.60 | 0.60 | 0.60 |
| Polyethylene glycol | 0.60 | 0.60 | 0.60 | 0.60 | 0.60 | 0.60 | 0.60 | 0.60 |
| 1% by mass aqueous dispersion liquid of oxidized cellulose nanofibers | 1.00 | 0.50 |  |  |  |  |  |  |
| 1% by mass aqueous dispersion liquid of carboxymethylated cellulose nanofibers |  |  | 0.50 |  |  |  |  |  |
| 1% by mass aqueous dispersion liquid of carboxymethylated cellulose nanofiber-containing composition (dried solid) |  |  |  | 0.50 |  |  |  |  |
| Xanthan gum |  |  |  |  |  | 0.2 |  |  |
| Hydroxyethyl cellulose |  |  |  |  |  |  | 0.1 | 0.01 |
| Total | 100 | 100 | 100 | 100 | 100 | 100 | 100 | 100 |
| Ejection state | ○ | ○ | ○ | ○ | ○ | ○ | ○ | ○ |
| Foam State | ○ | ○ | ○ | ○ | X | Δ | Δ | Δ |
| Elasticity of foam | ○ | ○ | ○ | ○ | X | Δ | X | Δ |
| Ease of foam-spreading on skin | ○ | ○ | ○ | ○ | X | Δ | Δ | Δ |
| Adsorptive ability to skin | ○ | ○ | ◎ | ◎ | X | X | ○ | ○ |

Polyoxyethylene phytostanol in Table 1 means polyoxyethylene phytostanol ether.

As is clear from Table 1, the foamable aerosol compositions of Examples 1 to 4 including cellulose nanofibers are continuously ejected from the container to form dense and uniform foam, and the formed foam has certain elasticity as well as is possible to easily spread onto the object (skin). In addition, the adsorptive ability of the foam to the object (skin) is good and the foam hardly drips from the object. With respect to the adsorptive ability of the foam to the object (skin), the carboxymethylated cellulose nanofibers are particularly good from the results of Examples 3 and 4. Although the compositions of Comparative Examples 1 to 4 that do not include cellulose nanofibers are continuously ejected from the container, both of the foam state and the elasticity of the foam are poor. These results indicate that the foamable aerosol composition of the present invention provides various performances required for the foamable aerosol composition at a high level all together while having sufficient suitability as an aerosol composition. In addition, it is indicated that the facial treatment mask of the present invention has good adsorbability to skin.

The invention claimed is:

1. A composition, comprising:
   a stock solution comprising a carboxymethylated cellulose nanofiber, a surfactant, and a fatty acid soap; and
   a propellant comprising liquefied natural gas,
   wherein a content ratio of the carboxymethylated cellulose nanofiber is from 0.001 to 0.05% by mass, and a content ratio of the fatty acid soap is from 1% by mass to 10% by mass, relative to a total amount of the stock solution,
   a content ratio of the propellant is from 1% by mass to 60% by mass, and a content ratio of the stock solution is from 40% by mass to 99% by mass, relative to a total amount of the composition,
   the fatty acid soap comprises stearic acid and behenic acid, and
   the composition is in the form of a foamable aerosol.

2. The composition according to claim 1, wherein the stock solution further comprises an oxidized cellulose nanofiber, and an amount of a carboxy group contained in the oxidized cellulose nanofiber is from 0.1 mmol/g to 3.0 mmol/g relative to a bone-dry mass of the oxidized cellulose nanofiber.

3. The composition according to claim 1, wherein a degree of substitution with carboxymethyl group per glucose unit in the carboxymethylated cellulose nanofiber is from 0.01 to 0.50.

4. The composition according to claim 1, wherein the foamable aerosol composition is a facial treatment mask.

5. A kit, comprising:
   an aerosol container; and
   the composition according to claim 1 filled in the aerosol container.

6. The composition according to claim 1, wherein an amount of the surfactant is from 0.05 to 10% by mass relative to the total amount of the stock solution.

7. The composition according to claim 1, wherein the stock solution is foamed and is not in a liquid form when ejected with the propellant.

8. The composition according to claim 1, wherein the content ratio of the carboxymethylated cellulose nanofiber is from 0.005 to 0.01% by mass, relative to the total amount of the stock solution.

9. The composition according to claim 1, wherein the content ratio of the carboxymethylated cellulose nanofiber is 0.005% by mass, relative to the total amount of the stock solution.

* * * * *